US010132774B2

(12) United States Patent
Akiyama et al.

(10) Patent No.: US 10,132,774 B2
(45) Date of Patent: Nov. 20, 2018

(54) GAS SENSOR CONTROL DEVICE

(71) Applicant: NGK SPARK PLUG CO., LTD., Nagoyai, Aichi (JP)

(72) Inventors: Yu Akiyama, Dusseldorf (DE); Yasuhiro Ishiguro, Novi, MI (US); Tomohisa Terui, Ichinomiya (JP); Kazuhisa Fujibayashi, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 639 days.

(21) Appl. No.: 14/397,793

(22) PCT Filed: Mar. 28, 2013

(86) PCT No.: PCT/JP2013/002121
§ 371 (c)(1),
(2) Date: Oct. 29, 2014

(87) PCT Pub. No.: WO2013/179545
PCT Pub. Date: Dec. 5, 2013

(65) Prior Publication Data
US 2015/0293053 A1    Oct. 15, 2015

(30) Foreign Application Priority Data

May 31, 2012    (JP) .................................. 2012-125400

(51) Int. Cl.
*G01N 27/419*    (2006.01)
*G01N 27/406*    (2006.01)
(Continued)

(52) U.S. Cl.
CPC ......... *G01N 27/419* (2013.01); *G01N 27/409* (2013.01); *G01N 27/4067* (2013.01);
(Continued)

(58) Field of Classification Search
None
See application file for complete search history.

(56) References Cited

U.S. PATENT DOCUMENTS

| | | | |
|---|---|---|---|
| 2011/0132775 A1* | 6/2011 | Kawai | F02D 41/146 205/784 |
| 2011/0147211 A1* | 6/2011 | Inagaki | F02D 41/042 204/406 |
| 2011/0290015 A1* | 12/2011 | Ishida | G01N 27/419 73/335.02 |

FOREIGN PATENT DOCUMENTS

| | | |
|---|---|---|
| JP | 2-276959 A | 11/1990 |
| JP | 6-265516 A | 9/1994 |

(Continued)

OTHER PUBLICATIONS

International Search Report for PCT/JP2013/002121 dated Jul. 2, 2013 English Translation.

*Primary Examiner* — Eli S Mekhlin
(74) *Attorney, Agent, or Firm* — Sughrue Mion, PLLC

(57) ABSTRACT

A gas sensor control apparatus (3) includes first current detection means for detecting a first pump current flowing between second electrodes (19, 20) in a state in which an object gas has become a prescribed gas supply state, the temperature of a sensor section (10f) has become a first target temperature, and the voltage between first electrodes (21, 22) has become a first target voltage; second current detection means for detecting a second pump current flowing between the second electrodes in a state in which the object gas has become the prescribed gas supply state, the temperature of the sensor section has become a second target temperature, and the voltage between the first electrodes has become a second target voltage; and $H_2O$ gas concentration (Continued)

detection means for detecting the $H_2O$ gas concentration of the object gas on the basis of the first and second pump currents.

8 Claims, 5 Drawing Sheets

(51) Int. Cl.
*G01N 27/409* (2006.01)
*G01N 27/41* (2006.01)
*G05B 15/02* (2006.01)
*G05D 7/06* (2006.01)

(52) U.S. Cl.
CPC .............. *G01N 27/41* (2013.01); *G05B 15/02* (2013.01); *G05D 7/0617* (2013.01)

(56) References Cited

FOREIGN PATENT DOCUMENTS

| | | |
|---|---|---|
| JP | 6-265518 A | 9/1994 |
| JP | 11-352101 A | 12/1999 |
| JP | 2009-075011 A | 4/2009 |
| JP | 2010-281732 A | 12/2010 |

* cited by examiner

GAS SENSOR CONTROL DEVICE

CROSS REFERENCE TO RELATED APPLICATIONS

This application is a National Stage of International Application No. PCT/JP2013/002121 filed Mar. 28, 2013, claiming priority based on Japanese Patent Application No. 2012-125400, filed May 31, 2012, the contents of all of which are incorporated herein by reference in their entirety.

TECHNICAL FIELD

The present invention relates to a gas sensor control apparatus (device) for controlling a gas sensor.

One of conventionally known gas sensors is a gas sensor which is disposed in an exhaust passage of an internal combustion engine (e.g., an automotive engine) so as to detect the oxygen concentration of exhaust gas. This gas sensor detects the oxygen concentration of exhaust gas to thereby detect the air-fuel ratio of exhaust gas by making use of a phenomenon that the magnitude of current flowing through a sensor element (a solid electrolyte body) changes with the oxygen concentration of exhaust gas.

Patent Document 1 describes such a gas sensor which includes a detection cell, a pump cell, and a heater for heating the cells. Also, Patent Document 1 describes a technique of detecting the $H_2O$ gas concentration of an object gas (gas under measurement) through use of a gas sensor control apparatus controlling the gas sensor, when the object gas is the atmosphere.

PRIOR ART DOCUMENT

Patent Document

Patent Document 1: Japanese Patent Application Laid-Open (kokai) No. 2010-281732

SUMMARY OF THE INVENTION

Problems to be Solved by the Invention

However, there has been demand for a technique of more properly detecting the $H_2O$ gas concentration of an object gas. The present invention has been accomplished in view of the present situation, and an object of the present invention is to provide a gas sensor control apparatus which can properly detect the $H_2O$ gas concentration of an object gas.

Means for Solving the Problems

One mode of the present invention is a gas sensor control apparatus for controlling a gas sensor which includes a sensor section and a heater for heating the sensor section, the sensor section having a detection cell which includes a first solid electrolyte body and a pair of first electrodes formed on the first solid electrolyte body, one of the first electrodes being disposed within a measurement chamber into which an object gas is introduced, and the other first electrode being exposed to an atmosphere having a reference oxygen concentration; and a pump cell which includes a second solid electrolyte body and a pair of second electrodes formed on the second solid electrolyte body, one of the second electrodes being disposed within the measurement chamber and which pumps out oxygen contained in the object gas introduced into the measurement chamber or pumps oxygen into the measurement chamber in accordance with pump current flowing between the pair of second electrodes. The gas sensor control apparatus comprises current control means for controlling the pump current flowing between the pair of second electrodes such that a voltage produced between the pair of first electrodes becomes equal to a target voltage; supply state judgment means for judging whether or not a supply state of the object gas is a prescribed gas supply state in which the object gas continuously has a prescribed oxygen concentration; heater control means for performing first heater control so as to control the heater such that temperature of the sensor section becomes a first target temperature at which the sensor section becomes active, when the supply state judgment means determines that the object gas is in the prescribed gas supply state, the heater control means performing second heater control so as to control the heater such that the temperature of the sensor section becomes a second target temperature higher than the first target temperature; voltage setting means for setting the target voltage to a first target voltage at which an $H_2O$ gas contained in the object gas does not dissociate substantially, when the supply state judgment means determines that the object gas is in the prescribed gas supply state, the voltage setting means setting the target voltage to a second target voltage which is higher than the first target voltage and at which an $H_2O$ gas contained in the object gas dissociates; first current detection means for detecting a first pump current flowing between the pair of second electrodes in a state in which the supply state of the object gas has become the prescribed gas supply state, the temperature of the sensor section has become the first target temperature, and the voltage between the pair of first electrodes has become the first target voltage; second current detection means for detecting a second pump current flowing between the pair of second electrodes in a state in which the supply state of the object gas has become the prescribed gas supply state, the temperature of the sensor section has become the second target temperature, and the voltage between the pair of first electrodes has become the second target voltage; and $H_2O$ gas concentration detection means for detecting the $H_2O$ gas concentration of the object gas on the basis of the first pump current and the second pump current.

In the above-described gas sensor control apparatus, the $H_2O$ gas concentration of the object gas is detected on the basis of the first pump current and the second pump current detected when the supply state of the object gas is the prescribed gas supply state. Specifically, the $H_2O$ gas concentration of the object gas is detected on the basis of, for example, a differential value obtained by subtracting the first pump current from the second pump current.

The first pump current is a current flowing between the pair of second electrodes of the pump cell detected when the voltage between the pair of first electrodes of the detection cell is set to a first target voltage (a voltage at which the $H_2O$ gas contained in the object gas does not dissociate substantially). Meanwhile, the second pump current is a current flowing between the pair of second electrodes detected when the voltage between the pair of first electrodes is set to a second target voltage (a voltage at which the $H_2O$ gas contained in the object gas dissociates).

Accordingly, the first pump current is a current detected in a state in which the $H_2O$ gas contained in the object gas does not dissociate on one of the first electrodes. Meanwhile, the second pump current is a current detected in a state in which the $H_2O$ gas contained in the object gas dissociates on the one first electrode (oxygen ions originating from the $H_2O$ gas are produced). Namely, the second pump current is greater than the first pump current by a current originating from the H$_2$O gas contained in the object gas. Accordingly, the H$_2$O gas concentration of the object gas can be detected on the basis of the first pump current and the second pump current.

In addition, in the above-described gas sensor control apparatus, the second pump current is detected in a state in which the temperature of the sensor section including the first and second solid electrolyte bodies is controlled to the second target temperature higher than the first target temperature (a temperature when the first pump current is detected).

As described above, when the second pump current is detected, the temperature of the sensor section is rendered higher than that at the time of detection of the first pump current. Thus, dissociation of the H$_2$O gas contained in the object gas can be promoted, as compared with the case where the temperature of the sensor section is not changed (the voltage between the first electrodes is assumed to be maintained at the same target voltage; i.e., the second target voltage). Moreover, the second pump current to be detected can be stabilized (a change in the second pump current due to a change in the voltage between the first electrodes controlled to the second target voltage can be made smaller). As a result, the detection accuracy of the H$_2$O gas concentration of the object gas can be increased as compared with the case where the second pump current is detected in a state in which the temperature of the sensor section is maintained at the first target temperature) (the temperature of the sensor section is not increased). Therefore, the above-described gas sensor control apparatus can detect the H$_2$O gas concentration of the object gas more properly.

Incidentally, it is known that, when the voltage between the first electrodes is increased, blackening becomes more likely to occur in the second solid electrolyte body (e.g., zirconia) of the sensor section. Blackening is a phenomenon that metal oxides contained in a solid electrolyte body are reduced and a metal is produced (e.g., $ZrO_2 \rightarrow Zr+O_2$). When blackening occurs in the second solid electrolyte body, the characteristic (ion conductivity) of the second solid electrolyte body deteriorates, and consequently, the sensor may fail to properly detect the H$_2$O gas concentration of the object gas.

In contrast, in the above-described gas sensor control apparatus, by increasing the temperature of the sensor section (to the second target temperature), the voltage between the first electrodes at which the second pump current becomes stable can be lowered as compared with the case where the second pump current is detected at the first target temperature. Accordingly, the above-described gas sensor control apparatus has the following advantageous effect. In the case where the requirement is securing the same detection accuracy as that when the second pump current is detected at the first target temperature, the second target voltage which is the target voltage can be lowered, as compared with the case where the second pump current is detected at the first target temperature. As a result, the possibility of occurrence of blackening in the second solid electrolyte body can be decreased. From this point of view as well, the above-described gas sensor control apparatus can detect the H$_2$O gas concentration of the object gas more properly.

Notably, an example of the case where the "supply state of the object gas becomes the prescribed gas supply state in which the oxygen concentration of the object gas continuously becomes the prescribed value set in advance" is a state in which exhaust gas (object gas) continuously becomes the atmosphere (air) due to fuel cut operation of an internal combustion engine, and the atmosphere is continuously supplied to the gas sensor. The atmosphere corresponds to the object gas whose oxygen concentration becomes the prescribed value set in advance. Another example of the case where the supply state of the object gas becomes the prescribed gas supply state is a state in which a vehicle stops so as to wait for a traffic light to change and an internal combustion engine mounted on the vehicle is brought into an idling state in which air-fuel ratio control is performed, whereby the exhaust gas (object gas) continuously has a prescribed A/F value (e.g., the theoretical air-fuel ratio), and such exhaust gas is continuously supplied to the gas sensor. This exhaust gas corresponds to the object gas whose oxygen concentration becomes the prescribed value set in advance.

The above-described gas sensor control apparatus is preferably configured such that the voltage setting means sets the target voltage to the second target voltage with a delay after the heater control means has started the second heater control.

As compared with the case where the temperature of the solid electrolyte body is the first target temperature, blackening of the solid electrolyte body (e.g., zirconia) is less likely to occur when the temperature of the solid electrolyte body is higher than the first target temperature. Incidentally, if the target voltage is set to the second target voltage by the voltage setting means before the second heater control is started by the heat control means, the voltage between the first electrodes is raised from the first target voltage to the second target voltage in a state in which the temperature of the sensor section including the second solid electrolyte body is the first target temperature, whereby the possibility of occurrence of blackening in the second solid electrolyte body increases.

In contrast, in the above-described gas sensor control apparatus, the target voltage is set to the second target voltage with a delay after the heater control means has started the second heater control. As a result, the voltage between the first electrodes is raised from the first target voltage to the second target voltage after the temperature of the sensor section including the second solid electrolyte body has become higher than the first target temperature as a result of start of the second heater control. Therefore, as compared with the case where the target voltage is set to the second target voltage before the second heater control is started by the heater control means, the possibility of occurrence of blackening in the second solid electrolyte body can be decreased.

The above-described gas sensor control apparatus is preferably configured such that the voltage setting means sets the target voltage to the second target voltage after the temperature of the sensor section has reached the second target temperature as a result of performance of the second heater control by the heater control means.

According to the above-described gas sensor control apparatus, the voltage between the first electrodes increases from the first target voltage toward the second target voltage after the temperature of the sensor section including the second solid electrolyte body has reached the second target temperature. Accordingly, the possibility of occurrence of blackening in the second solid electrolyte body can be decreased further.

Any one of the above-described gas sensor control apparatuses is preferably configured such that the second current detection means detects the second pump current in a state in which the temperature of the sensor section is stably maintained at the second target temperature as a result of performance of the second heater control by the heater control means.

When the temperature of the sensor section including the first and second solid electrolyte bodies is raised to the second target temperature by the second heater control of the heater control means, hunting may occur and increase the time required for the temperature of the sensor section to be stably controlled to the second target temperature. Therefore, in some situations, the second pump current needs a time to become stable after the temperature of the sensor section has been raised to the second target temperature.

In contrast, in the above-described gas sensor control apparatus, the second pump current is detected in a state in which the temperature of the sensor section is stably maintained at the second target temperature. Namely, the second pump current is detected after waiting until the temperature of the sensor section becomes stable at the second target temperature after having been raised to the second target temperature by the second heater control of the heater control means. Since the $H_2O$ gas concentration of the object gas can be detected on the basis of the stable second pump current, the detection accuracy can be increased further.

Notably, the "state in which the temperature of the sensor section is stably maintained at the second target temperature" refers to a state in which variation of the temperature of the sensor section falls within a temperature range of the second target temperature ±10 degrees.

MODE FOR CARRYING OUT THE INVENTION

Embodiment

Figure 1:
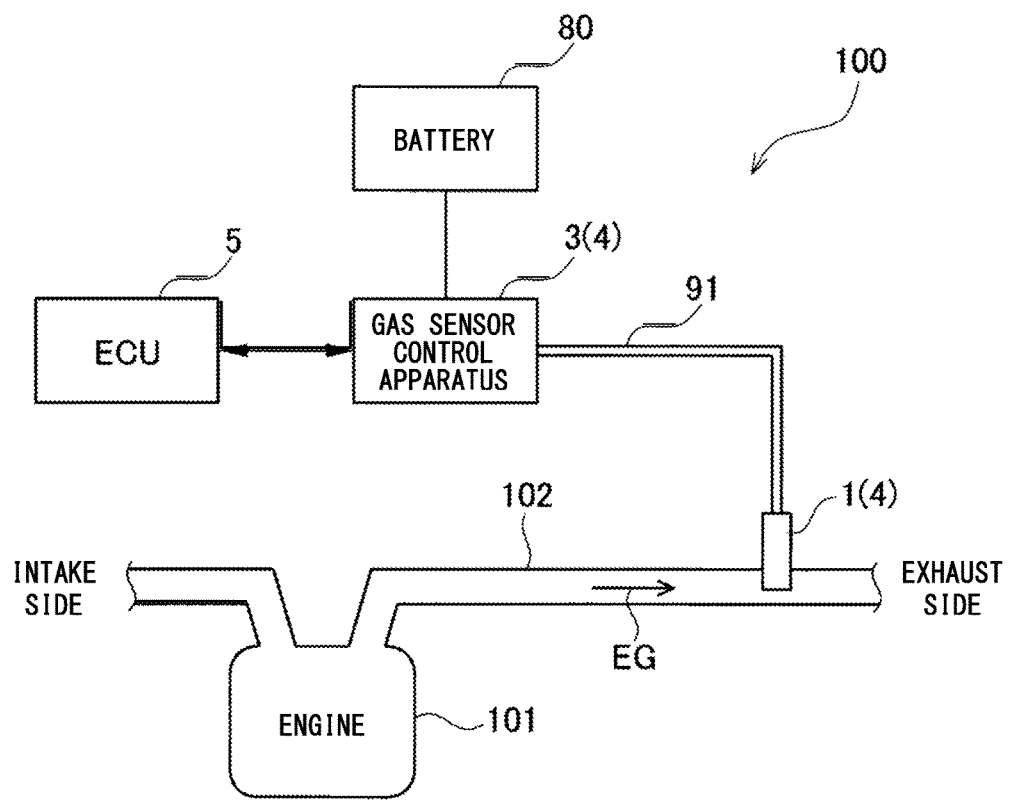
FIG. 1 Schematic diagram of an internal combustion engine according to an embodiment.

An embodiment of the present invention will next be described with reference to the drawings. FIG. 1 is a schematic diagram of an internal combustion engine system 100 according to the present embodiment. The internal combustion engine system 100 includes an engine 101 for propelling an automobile. An exhaust pipe 102 is connected to the engine 101 so as to discharge to the outside of the automobile exhaust gas EG (corresponding to the object gas) discharged from the engine 101. A full-range air-fuel-ratio sensor 1 (corresponding to the gas sensor) is disposed in an exhaust passage formed by the exhaust pipe 102. The exhaust gas EG discharged from the engine 101 is supplied to the full-range air-fuel-ratio sensor 1.

The full-range air-fuel-ratio sensor 1 (hereinafter, also referred to as the sensor 1 for simplicity) is a gas sensor for detecting the concentration of a specific component (oxygen in the present embodiment) contained in exhaust gas EG flowing through the exhaust passage formed by the exhaust pipe 102. The full-range air-fuel-ratio sensor 1 is connected, via a harness (signal wire) 91, to a sensor control apparatus 3, which is disposed at a position separated away from the sensor.

The gas sensor control apparatus 3 detects the oxygen concentration by energizing and controlling the sensor 1. Specifically, the gas sensor control apparatus 3 operates upon receipt of electric power from a battery 80, and outputs to an ECU (engine control unit) 5 a detection signal which represents the oxygen concentration detected by use of the sensor 1.

The ECU 5 is an apparatus for electronically controlling the operation of the engine 101 of the automobile. The ECU 5 is a microcomputer on which a CPU, a ROM, a RAM (which have known configurations and are not shown), etc. are mounted. The ECU 5 controls fuel injection timing and ignition timing by executing a control program. The ECU 5 receives, as information for performing such control, the output (detection signal) from the gas sensor control apparatus 3 which changes in accordance with the oxygen concentration of the exhaust gas EG. The ECU 5 also receives, as other pieces of information, signals from other sensors (for example, a signal representing crank angle from which the piston position and rotational speed of the engine 101 can be detected, a signal representing coolant temperature, and a signal representing combustion pressure).

Such an ECU 5 performs air-fuel ratio feedback control for the engine 101 on the basis of the output of the sensor 1. Also, the ECU 5 determines whether or not the state of supply of the exhaust gas EG from the engine 101 to the sensor 1 is a prescribed gas supply state.

The "prescribed gas supply state" refers to a state of supply of the exhaust gas EG from the engine 101 to the sensor 1 in which the exhaust gas EG continuously has a prescribed oxygen concentration predetermined in advance. In the present embodiment, the "prescribed gas supply state" is defined as follows. For example, when an automobile on which the internal combustion engine system 100 is mounted stops so as to wait for a traffic light to change, the engine 101 is brought into an idling state in which air-fuel ratio control is performed, whereby the exhaust gas EG continuously has a prescribed A/F ratio (e.g., the theoretical air-fuel ratio), and such exhaust gas EG is continuously supplied to the sensor 1. This state is defined as the "prescribed gas supply state." On the basis of the revived information, the ECU 5 determines, at predetermined intervals, whether or not the state of supply of the exhaust gas EG is the above-mentioned "prescribed gas supply state."

Figure 2:
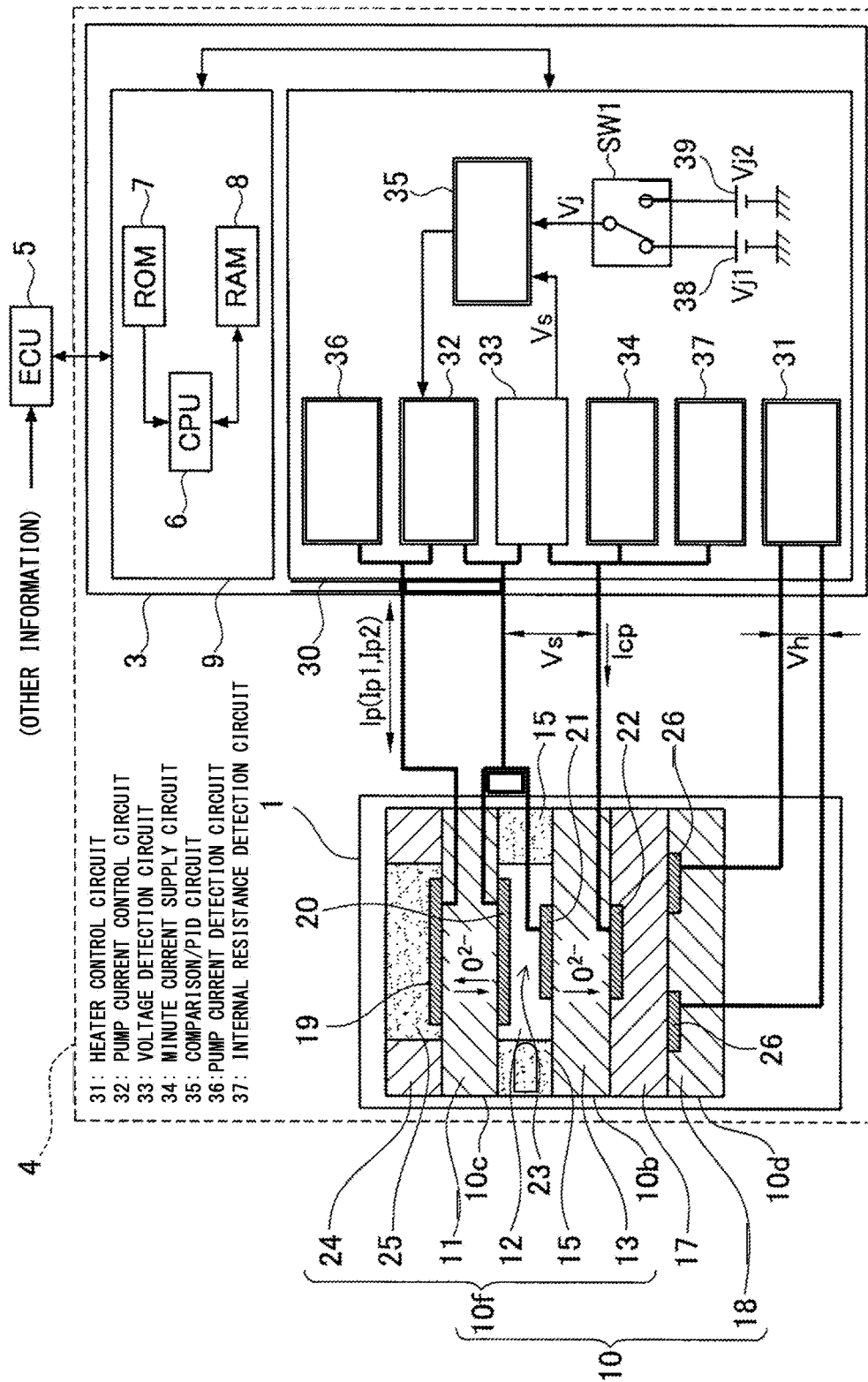
FIG. 2 Diagram of a gas sensor unit according to the embodiment.

Next, with reference to FIG. 2, the sensor 1 and the gas sensor control apparatus 3 will be described in detail. Notably, FIG. 2 is a diagram of a gas sensor unit 4 according to the present embodiment. The gas sensor unit 4 is composed of the sensor 1 and the gas sensor control apparatus 3.

The sensor 1 includes a sensor element 10 assuming the form of an elongated long plate, and an unillustrated housing which holds the sensor element 10 therein. The sensor element 10 includes first and second solid electrolyte bodies 13 and 11 mainly formed of zirconia, and insulating substrates 12, 17, 18, and 24 mainly formed of alumina. These members are stacked in the order of the insulating substrates 18 and 17, the first solid electrolyte body 13, the insulating substrate 12, the second solid electrolyte body 11, and the insulating substrate 24.

Paired second electrodes 19 and 20 mainly formed of platinum are formed on opposite sides of the second solid electrolyte body 11. Similarly, paired first electrodes 21 and 22 mainly formed of platinum are formed on opposite sides of the first solid electrolyte body 13. The first electrode 22 is sandwiched between the first solid electrolyte body 13 and the insulating substrate 17. Each of the first and second solid electrolyte bodies 13 and 11, and the insulating substrates 12, 17, 18, and 24 is formed in the shape of an elongated plate, and FIG. 2 shows cross sections of these members taken perpendicular to the longitudinal direction thereof.

At one end of the insulating substrate 12 with respect to the longitudinal direction thereof (direction perpendicular to the sheet of FIG. 2), there is formed a hollow measurement chamber 23, whose opposite wall surfaces are formed by corresponding surfaces of the first and second solid electrolyte bodies 13 and 11 and into which the exhaust gas EG can be introduced. Porous diffusion-rate-limiting sections 15 are provided at opposite ends of the measurement chamber 23 with respect to the width direction (the left-to-right direction in FIG. 2) so as to limit the flow rate of the exhaust gas EG introduced into the measurement chamber 23. The second electrode 20 on the second solid electrolyte body 11 and the first electrode 21 on the first solid electrolyte body 13 are exposed to the interior of the measurement chamber 23, and electrically communicate with each other.

The second electrode 19 on the second solid electrolyte body 11 is covered with a porous protection layer 25 formed of ceramic (for example, alumina). That is, this protection layer 25 prevents the second electrode 19 from deteriorating, which would otherwise be caused by poisoning components, such as silicon, contained in the exhaust gas EG. Notably, the insulating substrate 24 layered on the second solid electrolyte body 11 has an opening so that the insulating substrate 24 does not cover the second electrode 19, and the protection layer 25 is provided within the opening.

The second solid electrolyte body 11 and the pair of second electrodes 19 and 20 provided on the opposite surfaces thereof constitute a "pump cell 10c" which pumps oxygen into the measurement chamber 23 from the outside or pumps to the outside the oxygen contained in the exhaust gas EG introduced into the measurement chamber 23 (the exhaust gas EG) in accordance with a pump current Ip flowing between the second electrodes 19 and 20.

The first solid electrolyte body 13 and the pair of first electrodes 21 and 22 provided on the opposite surfaces thereof constitute a "detection cell 10b." The first electrode 22 functions as an oxygen reference electrode which maintains an oxygen concentration which serves as a reference for detection of the oxygen concentration within the measurement chamber 23. The first electrode 22 is exposed to an atmosphere having the reference oxygen concentration. Therefore, a voltage is generated between the first electrodes 21 and 22 of the detection cell 10b due to the difference between the concentration of oxygen ions produced on the first electrode 21 and the concentration of oxygen ions produced on the first electrode 22. The pump cell 10c and the detection cell 10b constitute a "sensor section 10f."

A heat generation resistor 26 mainly formed of platinum is sandwiched and buried between the insulating substrates 17 and 18. The insulating substrates 17 and 18, and the heat generation resistor 26 constitute a "heater 10d" for heating the sensor section 10f for activation.

Next, the gas sensor control apparatus 3 for controlling the sensor 1 (the sensor element 10) will be described in detail. The gas sensor control apparatus 3 is mainly composed of a microcomputer 9 and an electric circuit section 30. The microcomputer 9 is a microcomputer chip on which a CPU 6, a ROM 7, a RAM 8 (which have known configurations), etc. are mounted. Notably, the ROM 7 stores, for example, a control program for causing the CPU 6 to perform various types of processing.

The electric circuit section 30 is composed of a heater control circuit 31, a pump current control circuit 32, a voltage detection circuit 33, a minute current supply circuit 34, a comparison/PID circuit 35, a pump current detection circuit 36, and an internal resistance detection circuit 37.

The heater control circuit 31 supplies a voltage Vh to opposite ends of the heat generation resistor 26, while controlling the voltage through PWM, to thereby cause the heat generation resistor 26 to generate heat, thereby heating the sensor section 10f (the pump cell 10c including the second solid electrolyte body 11 and the detection cell 10b including the first solid electrolyte body 13). Specifically, the heater control circuit 31 controls the supply of electricity to the heater 10d (the heat generation resistor 26) such that the temperature T of the sensor section 10f becomes equal to a target temperature Tj.

In the present embodiment, two target temperatures (a first target temperature Tj1 and a second target temperature Tj2) are provided as the target temperature Tj. Of the two target temperatures, the first target temperature Tj1 is a temperature (830° C. in the present embodiment) at which the sensor section 10f becomes active. Meanwhile, the second target temperature Tj2 is a temperature (950° C. in the present embodiment) higher than the first target temperature Tj1.

Notably, in the present embodiment, the temperature T of the sensor section 10f is controlled by controlling the internal resistance Rs of the first solid electrolyte 13 contained in the sensor section 10f. Specifically, the first solid electrolyte 13 has a characteristic that its internal resistance Rs changes with its temperature, and the internal resistance Rs of the first solid electrolyte 13 has a correlation with the temperature thereof. In view this, the internal resistance Rs of the first solid electrolyte 13 is detected by the internal resistance detection circuit 37, and the temperature T of the sensor section 10f is controlled on the basis of the detected internal resistance Rs (with the temperature of the first solid electrolyte 13 considered as the temperature T of the sensor section 10f).

The internal resistance Rs of the first solid electrolyte 13 is detected as follows. First, a constant current I is caused to flow between the first electrodes 21 and 22 of detection cell 10b for a predetermined time through use of a constant current source circuit which constitutes the internal resistance detection circuit 37, and the voltage V between the first electrodes 21 and 22 which changes with the supply of the constant current I is detected though use of the internal resistance detection circuit 37. The CPU 6 of the microcomputer 9 computes the internal resistance Rs on the basis of the constant current I and a change in the voltage V due to supply of the constant current I. More specifically, the CPU 6 obtains, through the internal resistance detection circuit 37, a voltage between the first electrodes 21 and 22 measured before supply of the constant current I from the constant current source circuit contained in the internal resistance detection circuit 37 to the detection cell 10b, and a voltage between the first electrodes 21 and 22 measured when a predetermined time (e.g., 60 μs) has elapsed after the supply of the constant current I from the constant current source circuit to the detection cell 10b. The CUP 6 then detects the internal resistance Rs from the difference (change amount) ΔV between the obtained two voltages through use of a calculation formula or a map which is set in advance.

Accordingly, in the present embodiment, when the control of the gas sensor 1 by the gas sensor control apparatus 3 is started, the CPU 6 of the microcomputer 9 sets an internal resistance Rs corresponding to the first target temperature Tj1 (the internal resistance Rs of the first solid electrolyte 13 when the temperature T of the sensor section 10f has reached the first target temperature Tj1; this internal resistance Rs will be referred to as a first target internal resistance Rs1). Subsequently, the heater control circuit 31 controls the supply of electricity to the heat generation resistor 26 such that the internal resistance Rs of the first solid electrolyte 13 becomes equal to the first target internal resistance Rs1. As a result, the temperature T of the sensor section 10f is controlled to the first target temperature Tj1. In the present embodiment, this control will be referred to as a first heater control.

When the ECU 5 determines that the exhaust gas EG is in the prescribed gas supply state, the CPU 6 of the microcomputer 9 sets an internal resistance Rs corresponding to the second target temperature Tj2 (the internal resistance Rs of the first solid electrolyte 13 when the temperature T of the sensor section 10f has reached the second target temperature Tj2; this internal resistance Rs will be referred to as a second target internal resistance Rs2). Subsequently, the heater control circuit 31 controls the supply of electricity to the heat generation resistor 26 such that the internal resistance Rs of the first solid electrolyte 13 becomes equal to the second target internal resistance Rs2. As a result, the temperature T of the sensor section 10f is controlled to the second target temperature Tj2. In the present embodiment, this control will be referred to as a second heater control. Notably, in the present embodiment, the heater control circuit 31 and the microcomputer 9 correspond to the heater control means.

The minute current supply circuit 34 causes a very small current Icp to flow from the first electrode 22 of the detection cell 10b to the first electrode 21 thereof, to thereby move oxygen ions from the first electrode 21 to the first electrode 22, whereby an atmosphere having a reference oxygen concentration is produced in the porous first electrode 22. Thus, the first electrode 22 functions as an oxygen reference electrode, which serves as a reference for detection of the oxygen concentration of the exhaust gas EG.

The voltage detection circuit 33 detects the voltage Vs between the first electrodes 21 and 22 of the detection cell 10b. The comparison/PID circuit 35 compares the target voltage Vj set by the CPU 6 of the microcomputer 9 with the voltage Vs detected by the voltage detection circuit 33. The comparison/PID circuit 35 produces a control instruction value on the basis of the result of the comparison and through use of a PID control method. The control instruction value is input to the pump current control circuit 32 so as to control the magnitude and direction of the pump current Ip flowing between the second electrodes 19 and 20 of the pump cell 10c such that the voltage Vs between the first electrodes 21 and 22 becomes equal to the target voltage Vj.

The pump current control circuit 32 controls the magnitude and direction of the pump current Ip flowing between the second electrodes 19 and 20 of the pump cell 10c, on the basis of the comparison result obtained from the comparison/PID circuit 35, such that the voltage Vs between the first electrodes 21 and 22 becomes equal to the target voltage Vj. As a result, the pump cell 10c pumps oxygen into the measurement chamber 23 or pumps oxygen out of the measurement chamber 23. The pump current detection circuit 36 detects the pump current Ip flowing between the second electrodes 19 and 20 of the pump cell 10c.

In the present embodiment, two target voltages (the first and second target voltages Vj1 and Vj2) can be set to be used as the target voltage Vj to be compared with the voltage Vs by the compression/PID circuit 35. Specifically, the electric circuit section 30 has a first reference power supply 38 and a second reference power supply 39 connected to the comparison/PID circuit 35 through a switch SW1. The voltage of the first reference power supply 38 is set to the first target voltage Vj1, and the voltage of the second reference power supply 39 is set to the second target voltage Vj2. Therefore, the target voltage Vj can be set to the first target voltage Vj1 by switching the switch SW1 to the first reference power supply 38 side. Meanwhile, the target voltage Vj can be set to the second target voltage Vj2 by switching the switch SW1 to the second reference power supply 39 side.

Notably, the first target voltage Vj1 is set to a voltage value (450 mV in the present embodiment) determined such that, when the voltage Vs becomes equal to the first target voltage Vj1, the $H_2O$ gas contained in the exhaust gas EG in the measurement chamber 23 does not dissociate substantially on the first electrode 21, although the oxygen gas contained in the exhaust gas EG dissociates on the first electrode 21. Meanwhile, the second target voltage Vj2 is set to a voltage value (1000 mV in the present embodiment) determined such that, when the voltage Vs becomes equal to the second target voltage Vj2, not only the oxygen gas contained in the exhaust gas EG in the measurement chamber 23 but also the $H_2O$ gas dissociates on the first electrode 21.

In the present embodiment, when the control of the sensor 1 by the gas sensor control apparatus 3 is started, the microcomputer 9 selects the first target voltage Vj1 as the target voltage Vj. Specifically, the microcomputer 9 switches the switch SW1 to the first reference power supply 38 side to thereby set the target voltage Vj to the first target voltage Vj1. Subsequently, the pump current Ip is controlled by the pump current control circuit 32 such that the voltage Vs between the first electrodes 21 and 22 becomes equal to the first target voltage Vj1. At that time, the temperature T of the sensor section 10f is controlled to the first target temperature Tj1 as described above. In this state, the microcomputer 9 detects (calculates) the oxygen concentration of the exhaust gas EG on the basis of the pump current Ip.

After that, when the ECU 5 determines that the supply state of the exhaust gas EG is the prescribed gas supply state in a state in which the temperature T of the sensor section 10f has become equal to the first target temperature Tj1 and the voltage Vs between the first electrodes 21 and 22 has become equal to the first target voltage Vj1, the pump current detection circuit 36 detects a first pump current Ip1 as the pump current Ip.

Further, when the temperature T of the sensor section 10f has become equal to the second target temperature Tj2 and the voltage Vs between the first electrodes 21 and 22 has become equal to the second target voltage Vj2 in the prescribed gas supply state, the pump current detection circuit 36 detects a second pump current Ip2 as the pump current Ip. Notably, in the present embodiment, the pump current detection circuit 36 corresponds to the first current detection means and the second current detection means.

The microcomputer 9 detects the $H_2O$ gas concentration of the exhaust gas EG on the basis of the first pump current Ip1 and the second pump current Ip2. Specifically, the microcomputer 9 detects the $H_2O$ gas concentration of the exhaust gas EG on the basis of a differential value $\Delta Ip$ (mA) obtained by subtracting the first pump current Ip1 from the second pump current Ip2. Notably, in the present embodiment, the "current control means" is constituted by the pump current control circuit 32, the voltage detection circuit 33, and the comparison/PID circuit 35.

Next, the flow of detecting the oxygen concentration (air-fuel ratio) of the exhaust gas EG will be described. Notably, when the oxygen concentration of the exhaust gas EG is detected, the first target voltage Vj1 (450 mV) is selected as the target voltage Vj which is used for comparison by the comparison/PID circuit 35. Further, the first target internal resistance Rs1 (the internal resistance Rs of the first solid electrolyte 13 at the time when the temperature T of the first solid electrolyte 13 becomes equal to the first target temperature Tj1) is used as the target internal resistance Rsj of the heater control circuit 31.

As shown in FIG. 2, the minute current supply circuit 34 first causes a very small current Icp to flow from the first electrode 22 of the detection cell 10b toward the first electrode 21 thereof. As a result of this, oxygen contained in the exhaust gas EG is pumped from the first electrode 21 side to the first electrode 22 side through the first solid electrolyte body 13, and the first electrode 22 functions as an oxygen reference electrode.

Next, the voltage detection circuit 33 detects the voltage Vs between the first electrodes 21 and 22. Subsequently, the comparison/PID circuit 35 compares the detected voltage Vs with the first target voltage Vj1. Next, the pump current control circuit 32 controls the magnitude and direction of the pump current Ip flowing between the second electrodes 19 and 20 of the pump cell 10c on the basis of the result of the comparison by the comparison/PID circuit 35 such that the voltage Vs becomes equal to the first target voltage Vj1.

Notably, in the case where the air-fuel ratio of the exhaust gas EG having flowed into the measurement chamber 23 is on the rich side of the theoretical air-fuel ratio, since the oxygen concentration of the exhaust gas EG is low, the pump current Ip flowing between the second electrodes 19 and 20 is controlled such that the pump cell 10c pumps oxygen into the measurement chamber 23 from the outside. Meanwhile, when the air-fuel ratio of the exhaust gas EG having flowed into the measurement chamber 23 is on the lean side of the theoretical air-fuel ratio, since a large amount of oxygen exists in the exhaust gas EG, the pump current Ip flowing between the second electrodes 19 and 20 is controlled such that the pump cell 10c pumps oxygen out of the measurement chamber 23 to the outside.

The pump current detection circuit 36 detects the pump current Ip at that time, and outputs it to the ECU 5. The ECU 5 determines the oxygen concentration of the exhaust gas EG (that is, the air-fuel ratio of the exhaust gas EG) on the basis of the magnitude and direction of the pump current Ip output from the pump current detection circuit 36. In this manner, the oxygen concentration of the exhaust gas EG (the air-fuel ratio of the exhaust gas EG) is detected.

As described above, the gas sensor control apparatus 3 of the present embodiment usually detects the oxygen concentration of the exhaust gas EG by using the sensor 1 every time a predetermined timing comes. However, in the case where the supply state of the exhaust gas EG is the prescribed gas supply state, the gas sensor control apparatus 3 of the present embodiment detects the $H_2O$ gas concentration of the exhaust gas EG by using the sensor 1.

Next, the detection of the $H_2O$ gas concentration performed by the gas sensor control apparatus 3 will be described with reference to FIGS. 3A and 3B. A program for executing the processing shown in FIGS. 3A and 3B ($H_2O$ gas concentration detection processing) is stored in the ROM 7 (see FIG. 2) of the microcomputer 9, and is executed by the CPU 6. The processing shown in FIGS. 3A and 3B is executed when the microcomputer 9 receives from the ECU 5 a signal indicating that the supply state of the exhaust gas EG is the "prescribed gas supply state" in a period during which the internal combustion engine system 100 is operating.

Figure 3A:
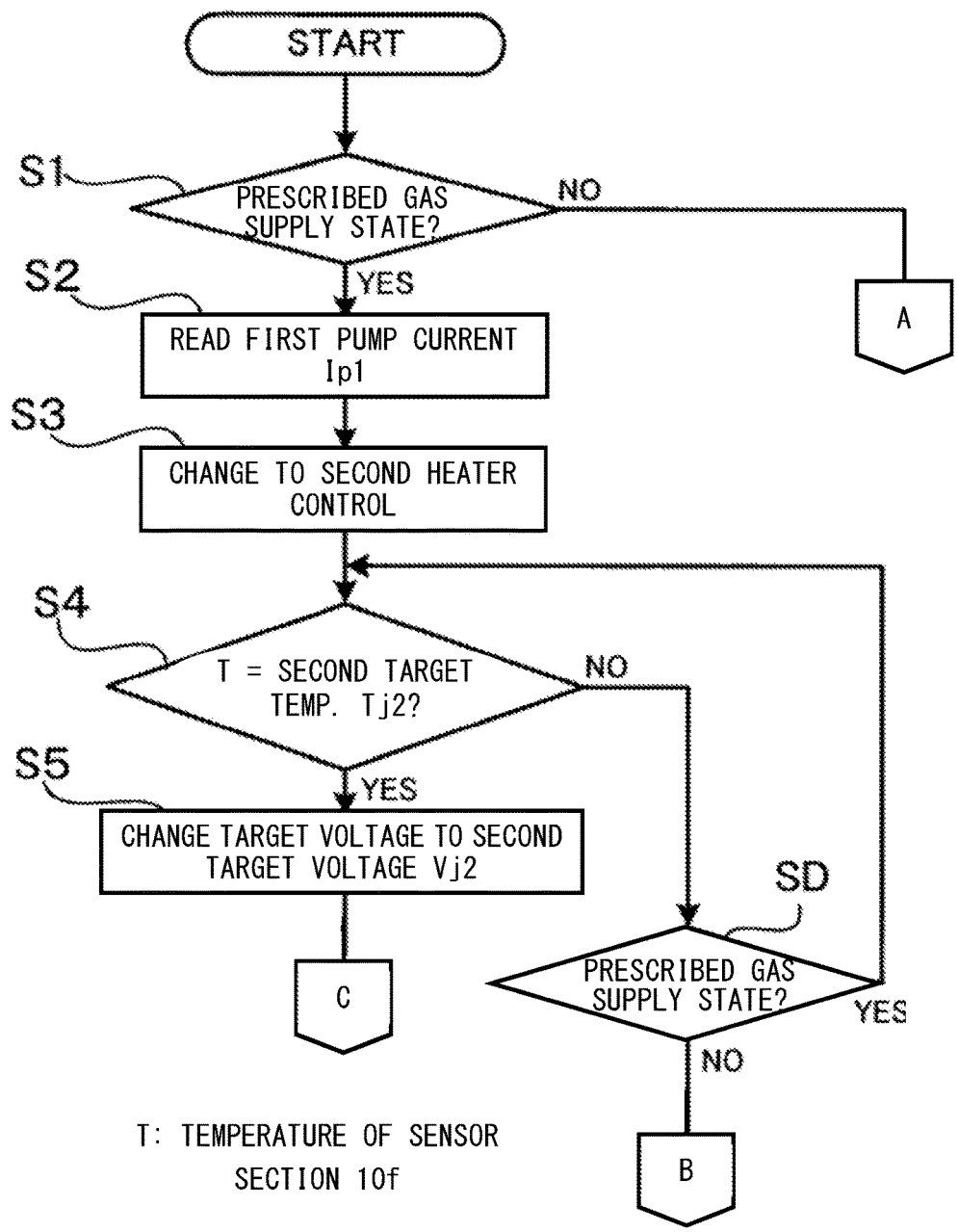
FIGS. 3A, 3B Flowcharts showing detection of $H_2O$ gas concentration according to the embodiment.
Figure 3B:
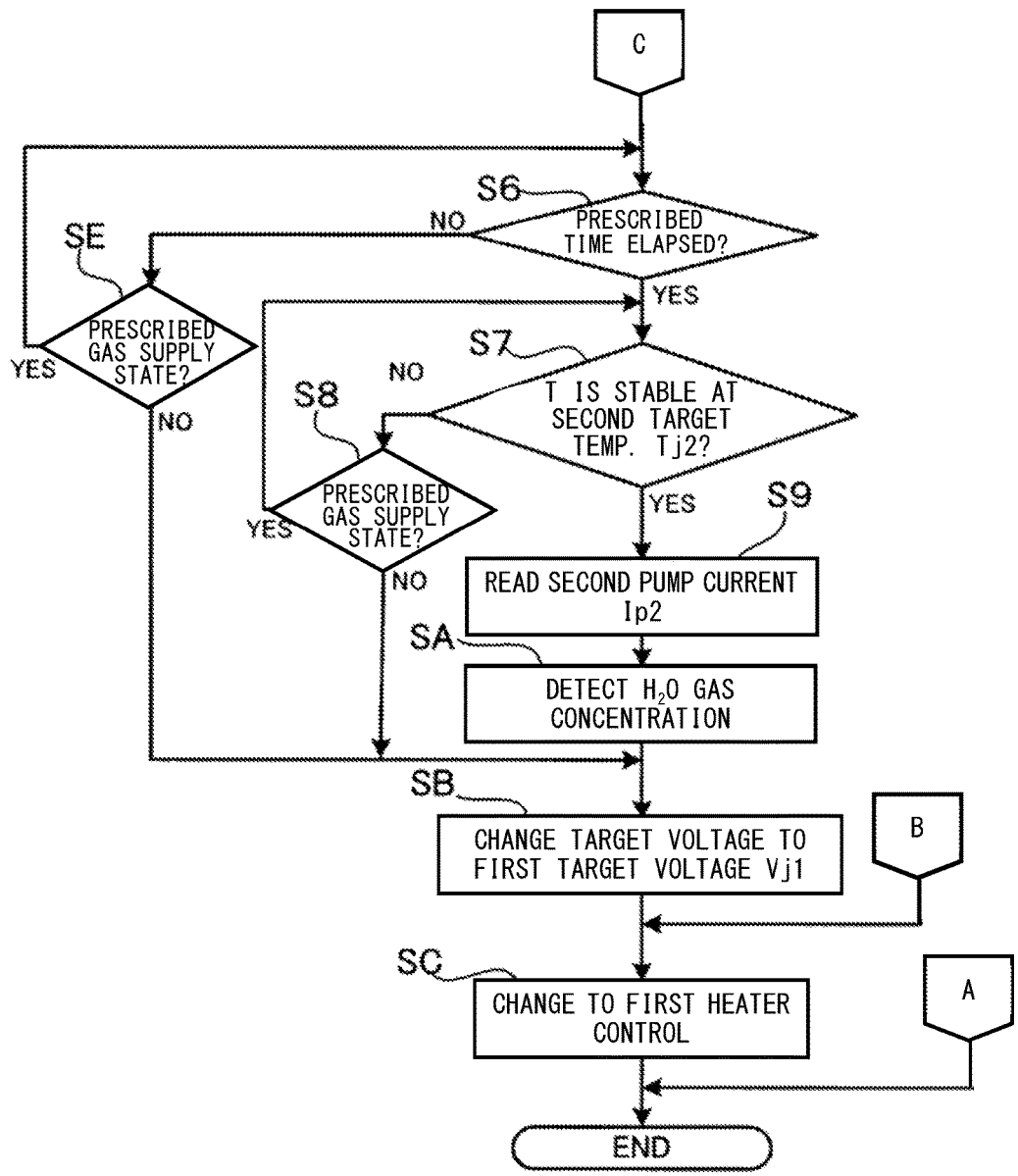

In a stage before the processing shown in FIGS. 3A and 3B is executed, the above-described oxygen concentration detection has been performed in the gas sensor control apparatus 3, and the target voltage Vj of the comparison/PID circuit 35 has been set to first target voltage Vj1 (450 mV), whereby the voltage Vs between the first electrodes 21 and 22 has become equal to the first target voltage Vj1 (450 mV). Moreover, the target internal resistance Rsj of the heater control circuit 31 has been set to the first target internal resistance Rs1 (the internal resistance Rs of the first solid electrolyte 13 at the time when the temperature T of the sensor section 10f becomes equal to the first target temperature Tj1), whereby the temperature T of the sensor section 10f has become equal to the first target temperature Tj1.

In step S1, the microcomputer 9 determines whether or not the supply state of the exhaust gas EG is the prescribed gas supply state. Specifically, the microcomputer 9 determines whether or not the state of supply of the exhaust gas EG (object gas) from the engine 101 to the sensor 1 is a supply state in which the exhaust gas EG continually has a prescribed oxygen concentration set in advance. More specifically, the microcomputer 9 determines whether or not the exhaust gas EG is continuously supplied to the sensor 1 in a state in which the engine 101 is brought into an idling state in which air-fuel ratio control is performed, because the automobile on which the internal combustion engine system 100 is mounted stops so as to wait for a traffic light to change, whereby the exhaust gas EG continuously has a prescribed A/F ratio (e.g., the theoretical air-fuel ratio).

In the present embodiment, the ECU 5 determines whether or not the supply state of the exhaust gas EG is the above-described "prescribed gas supply state" on the basis of information input from various sensors, etc. Specifically, when the engine 101 of the automobile is operating, the shift range position is in the D range, and the vehicle speed is zero, it can be determined that the engine 101 is in the idling state in which air-fuel ratio control is performed, for example, because the automobile stops so as to wait for a traffic light to change. Therefore, in this case, the ECU 5 detects that the supply state of the exhaust gas EG is the "prescribed gas supply state."

When the ECU 5 determines that the supply state of the exhaust gas EG is the "prescribed gas supply state," the ECU 5 sends to the microcomputer 9 a signal indicating that the supply state of the exhaust gas EG is the "prescribed gas supply state." When the microcomputer 9 receives this signal, the microcomputer 9 determines that the supply state of the exhaust gas EG is the "prescribed gas supply state" (YES). When the microcomputer 9 does not receive the signal, the microcomputer 9 determines that the supply state of the exhaust gas EG is not the "prescribed gas supply state" (NO).

In the case where the microcomputer 9 determines in step S1 that the supply state of the exhaust gas EG is not the "prescribed gas supply state" (NO), the microcomputer 9 ends the present program without performing the $H_2O$ gas concentration detection processing. Meanwhile, in the case where the microcomputer 9 determines in step S1 that the supply state of the exhaust gas EG is the "prescribed gas supply state" (YES), the microcomputer 9 proceeds step S2, and reads the first pump current Ip1 output from the pump current detection circuit 36. The value of the read first pump current Ip1 is stored in the RAM 8.

Notably, at that time, the target voltage Vj of the comparison/PID circuit 35 is still set to the first target voltage Vj1 (450 mV), and the target internal resistance Rsj of the heater control circuit 31 is still set to the first target internal resistance Rs1. Accordingly, the first pump current Ip1 is detected in a state in which the temperature T of the sensor section 10f has reached the first target temperature Tj1 (830° C.), and the voltage Vs between the first electrodes 21 and 22 have become equal to the first target voltage Vj1 (450 mV).

Next, the microcomputer 9 proceeds to step S3, and changes the target internal resistance Rsj of the heater control circuit 31 to the second target internal resistance Rs2 (the internal resistance Rs of the first solid electrolyte 13 at the time when the temperature T of the sensor section 10f is equal to the second target temperature Tj2). Namely, the microcomputer 9 changes the heater control by the heater control circuit 31 to the second heater control. As a result, the temperature T of the sensor section 10f is controlled to the second target temperature Tj2.

Next, the microcomputer 9 proceeds to step S4, and determines whether or not the temperature T of the sensor section 10f has reached the second target temperature Tj2 (950° C.). Specifically, the microcomputer 9 determines whether or not the internal resistance Rs of the first solid electrolyte 13 has decreased to the second target internal resistance Rs2.

In the case where the microcomputer 9 determines in step S4 that the temperature T of the sensor section 10f has not yet reached the second target temperature Tj2 (NO), the microcomputer 9 proceeds to step SD, and determines whether or not the supply state of the exhaust gas EG is still the prescribed gas supply state. Specifically, in the case where the microcomputer 9 continuously receives from the ECU 5 a signal indicating that the supply state of the exhaust gas EG is the "prescribed gas supply state," the microcomputer 9 determines that the supply state of the exhaust gas EG is the "prescribed gas supply state" (YES). Meanwhile, in the case where the microcomputer 9 does not receive from the ECU 5 the signal indicating that the supply state of the exhaust gas EG is the "prescribed gas supply state," the microcomputer 9 determines that the supply state of the exhaust gas EG is not the "prescribed gas supply state" (NO).

In the case where the microcomputer 9 determines that the supply state of the exhaust gas EG is not the prescribed gas supply state (NO), the microcomputer 9 proceeds to step SC, and changes the target internal resistance Rsj of the heater control circuit 31 to the first target internal resistance Rs1. With this processing, the microcomputer 9 changes the heater control by the heater control circuit 31 to the first heater control. After that, the microcomputer 9 ends the series of processing steps.

Meanwhile, in the case where the microcomputer 9 determines in step SD that the supply state of the exhaust gas EG is the prescribed gas supply state (YES), the microcomputer 9 returns to step S4, and determines whether or not the temperature T of the sensor section 10f has reached the second target temperature Tj2 (950° C.)

In the case where the microcomputer 9 determines in step S4 that the temperature T of the sensor section 10f has reached the second target temperature Tj2 (YES), the microcomputer 9 proceeds to step S5, and switches the switch SW1 of the electric circuit section 30 to the second reference power supply 39 side, to thereby change the target voltage Vj of the comparison/PID circuit 35 from the first target voltage Vj1 to the second target voltage Vj2 (1000 mV in the present embodiment). As a result, control of the pump current Ip is started by the pump current control circuit 32 such that the voltage Vs becomes equal to the second target voltage Vj2.

After that, the microcomputer 9 proceeds to step S6, and determines whether or a prescribed time has elapsed after it changed the target voltage Vj to the second target voltage Vj2. The prescribed time is a time required for the voltage Vs between the first electrodes 21 and 22 to become stable at the second target voltage Vj2, as a result of the control of the pump current Ip by the pump current control circuit 32, after the target voltage Vj was changed to the second target voltage Vj2. This prescribed time has been empirically determined in advance and stored in the ROM 7 of the microcomputer 9.

In the case where the microcomputer 9 determines in step S6 that the prescribed time has not yet elapsed (NO), the microcomputer 9 proceeds to step SE, and determines whether or not the supply state of the exhaust gas EG is the prescribed gas supply state as in the case of the previously mentioned step SD. In the case where the microcomputer 9 determines in step SE that the supply state of the exhaust gas EG is not the prescribed gas supply state (NO), the microcomputer 9 proceeds to step SB, and switches the switch SW1 of the electric circuit section 30 to the first reference power supply 38 side, to thereby return the target voltage Vj to the first target voltage Vj1. Further, the microcomputer 9 proceeds to step SC, and returns the target internal resistance Rsj of the heater control circuit 31 to the first target internal resistance Rs1. With this processing, the microcomputer 9 changes the heater control to the first heater control. After that, the microcomputer 9 ends the series of the processing steps. Meanwhile, in the case where the microcomputer 9 determines in step SE that the supply state of the exhaust gas EG is the prescribed gas supply state (YES), the microcomputer 9 returns step S6, and performs the above-described processing.

In the case where the microcomputer 9 determines in step S6 that the prescribed time has elapsed (YES), the microcomputer 9 proceeds to step S7, and determines whether or not the temperature T of the sensor section 10f is stably maintained at the second target temperature Tj2. Specifically, the microcomputer 9 determines whether or not the internal resistance Rs of the first solid electrolyte 13 detected by the electric circuit section 30 is stably maintained at the second target internal resistance Rs2.

In the case where the microcomputer 9 determines in step S7 that the temperature T of the sensor section 10f is not stably maintained at the second target temperature Tj2 (NO), the microcomputer 9 proceeds to step S8, and determines whether or not the supply state of the exhaust gas EG is the prescribed gas supply state as in the case of the previously described step SD. In the case where the microcomputer 9 determines in step S8 that the supply state of the exhaust gas EG is not the prescribed gas supply state (NO), the microcomputer 9 proceeds to step SB, and switches the switch SW1 of the electric circuit section 30 to the first reference power supply 38 side, to thereby return the target voltage Vj to the first target voltage Vj1. Further, the microcomputer 9 proceeds to step SC, and returns the target internal resistance Rsj of the heater control circuit 31 to the first target internal resistance Rs1. After that, the microcomputer 9 ends the series of the processing steps. Meanwhile, in the case where the microcomputer 9 determines in step S8 that the supply state of the exhaust gas EG is the prescribed gas supply state (YES), the microcomputer 9 returns step S7, and performs the above-described processing.

In the case where the microcomputer 9 determines in step S7 that the temperature T of the sensor section 10f is stably maintained at the second target temperature Tj2 (YES), the microcomputer 9 proceeds to step S9. In step S9, the microcomputer 9 reads the value of the second pump current Ip2 output from the pump current detection circuit 36, and stores it in the RAM 8.

Notably, at that time, the voltage Vs between the first electrodes 21 and 22 is stably maintained at the second target voltage Vj2. Also, the temperature T of the sensor section 10f is stably maintained at the second target temperature Tj2. Accordingly, the second pump current Ip2 is detected in a state in which the temperature T has reached the second target temperature Tj2 (950° C.) and the voltage Vs has become equal to the second target voltage Vj2 (1000 mV).

Notably, in the present embodiment, a state in which variation of the temperature T of the sensor section 10f falls within a temperature range of the second target temperature Tj2±10 degrees is considered as the state in which the temperature T of the sensor section 10f is stably maintained at the second target temperature Tj2. This state corresponds to a state in which variation of the internal resistance Rs of the first solid electrolyte 13 falls within a range of the second target internal resistance Rs2±10Ω. Accordingly, in step S7, the microcomputer 9 determines whether or not variation of the internal resistance Rs is within the range of the second target internal resistance Rs2±10Ω.

Next, the microcomputer 9 proceeds to step S9, and detects the $H_2O$ gas concentration of the exhaust gas EG on the basis of the first pump current Ip1 and the second pump current Ip2. Specifically, the microcomputer 9 detects the $H_2O$ gas concentration of the exhaust gas EG on the basis of the differential value ΔIp (mA) obtained by subtracting the first pump current Ip1 from the second pump current Ip2.

Notably, in the present embodiment, the correlation between the $H_2O$ gas concentration (%) of the exhaust gas EG and the differential value ΔIp (mA) has been empirically determined in advance, and a correlation function or a map representing the correlation between the $H_2O$ gas concentration (%) and the differential value ΔIp (mA) has been stored in the ROM 7 of the microcomputer 9. Accordingly, the CPU 6 of the microcomputer 9 can detect the $H_2O$ gas concentration of the exhaust gas EG from the differential value ΔIp (mA) by making use of the correlation function or the map.

Incidentally, the first pump current Ip1 is a current detected in a state in which the $H_2O$ gas contained in the exhaust gas EG does not dissociate substantially on the first electrode 21. Meanwhile, the second pump current Ip2 is a current detected in a state in which the $H_2O$ gas contained in the exhaust gas EG dissociates on the first electrode 21 (oxygen ions originating from the $H_2O$ gas are produced). Namely, the second pump current Ip2 is greater than the first pump current Ip1 by a current originating from the $H_2O$ gas contained in the exhaust gas EG. Accordingly, the $H_2O$ gas concentration of the exhaust gas EG can be detected on the basis of the first pump current Ip1 and the second pump current Ip2.

In addition, in the present embodiment, the second pump current Ip2 is detected in a state in which the temperature T of the sensor section 10f is controlled to the second target temperature Tj2 higher than the first target temperature Tj1 (the temperature when the first pump current Ip1 is detected).

As described above, when the second pump current Ip2 is detected, the temperature T of the sensor section 10f is rendered higher than that at the time of detection of the first pump current Ip1. Thus, dissociation of the $H_2O$ gas contained in the exhaust gas EG can be promoted, as compared with the case where the temperature T is not changed (is maintained at the first target temperature Tj1; notably, the voltage Vs between the first electrodes 21 and 22 is assumed to be maintained at the same target voltage; i.e., the second target voltage Vj2). Moreover, the second pump current Ip2 to be detected can be stabilized (a change in the second pump current Ip2 due to a change in the voltage Vs controlled to the second target voltage Vj2 can be made smaller).

Figure 4:
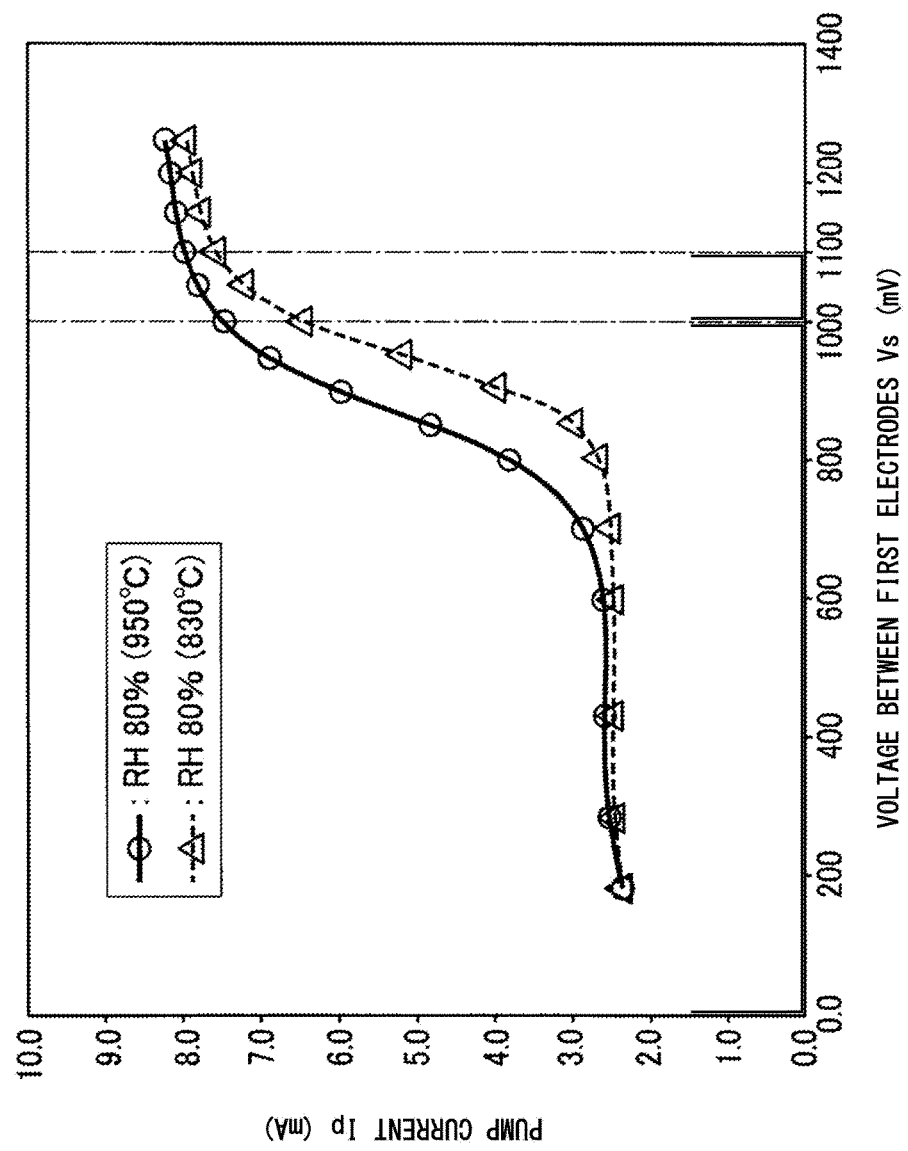
FIG. 4 Graph showing the correlation between pump current and voltage between first electrodes.

FIG. 4 shows the correlation between the pump current Ip and the voltage Vs between the first electrodes 21 and 22. In FIG. 4, the values of the pump current Ip measured in a state in which the A/F ratio was set to the theoretical air-fuel ratio and the temperature T of the sensor section 10f was maintained at 830° C. (the first target temperature Tj1) in an environment whose relative humidity was 80% are represented by triangular marks. A correlation curve connecting these marks is represented by a broken line. Meanwhile, the values of the pump current Ip measured in a state in which the A/F ratio was set to the theoretical air-fuel ratio and the temperature T of the sensor section 10f was maintained at 950° C. (the second target temperature Tj2) in the environment whose relative humidity was 80% are represented by circular marks. A correlation curve connecting these marks is represented by a continuous line.

As can be understood from FIG. 4, when comparison is made in the state in which the voltage Vs between the first electrodes 21 and 22 is fixed to 1000 mV (the target voltage Vj), in the case where the pump current Ip is detected with the temperature T of the sensor section 10f set to 950° C. (the second target temperature Tj2), the inclination (rate of change) of the curve becomes smaller as compared with the case where the pump current Ip is detected with the temperature T set to 830° C. (the first target temperature Tj1). Accordingly, even when the voltage Vs between the first electrodes 21 and 22 is the same (1000 mV (the second target voltage Vj2)), in the case where the pump current Ip is detected with the temperature T of the sensor section 10f set to 950° C. (the second target temperature Tj2), the measured value of the pump current Ip becomes more stable (a change in the pump current Ip stemming from a change in the voltage Vs becomes smaller), as compared with the case where the pump current Ip is detected with the temperature T set to 830° C. (the first target temperature Tj1).

As a result, the detection accuracy of the $H_2O$ gas concentration of the exhaust gas EG can be increased as compared with the case where not only the first pump current Ip1 but also the second pump current Ip2 is detected in a state in which the temperature T is maintained at 830° C. (the first target temperature Tj1) (the temperature T is not increased). Therefore, according to the present embodiment, the $H_2O$ gas concentration of the exhaust gas EG can be detected more properly.

Incidentally, it is known that, when the voltage Vs between the first electrodes 21 and 22 is increased, blackening becomes more likely to occur in the second solid electrolyte body 11. Blackening is a phenomenon that metal oxides contained in a solid electrolyte body are reduced and a metal is produced ($ZrO_2 \rightarrow Zr+O_2$). When blackening occurs in the second solid electrolyte body 11, the characteristic (ion conductivity) of the second solid electrolyte body 11 deteriorates, and consequently, the sensor 1 may fail to properly detect the $H_2O$ gas concentration of the exhaust gas EG.

In contrast, in the gas sensor control apparatus 3 of the present embodiment, by increasing the temperature T of the sensor section 10f (to the second target temperature Tj2), the voltage between the first electrodes 21 and 22 at which the second pump current Ip2 becomes stable can be lowered as compared with the case where the second pump current Ip2 is detected at the first target temperature Tj1.

This will be described specifically with reference to FIG. 4. The inclination (rate of change) of the curve obtained with the target temperature set to 950° C., the inclination being determined at a point where the voltage Vs=1000 mV, is the same as the inclination (rate of change) of the curve obtained with the target temperature set to 830° C., the inclination being determined at a point where the voltage Vs=1100 mV. Accordingly, in the case where the requirement is securing the same detection accuracy as that when the second pump current Ip2 is detected with the target temperature Tj set to 830° C. (the first target temperature Tj1) and the target voltage Vj set to 1100 mV, the target voltage Vj (the second target voltage Vj2) can be lowered to 1000 mV when the target temperature Tj is set to 950° C. (the second target temperature Tj2).

Namely, in the gas sensor control apparatus 3 of the present embodiment, in the case where the requirement is securing the same detection accuracy as that when the second pump current Ip2 is detected with the target temperature Tj maintained at the first target temperature Tj1, by controlling the temperature T of the sensor section 10f to a higher temperature (the second target temperature Tj2), the second target voltage Vj2 for the voltage Vs can be lowered as compared with the case where the second pump current Ip2 is detected with the target temperature Tj maintained at the first target temperature Tj1. As a result, the possibility of occurrence of blackening in the second solid electrolyte body 11 can be decreased. Even in the case where the second target voltage Vj2 is lowered, the $H_2O$ gas concentration of the exhaust gas EG can be detected properly.

After that, the microcomputer 9 proceeds to step SB, and returns the target voltage Vj to the first target voltage Vj1. Further, the microcomputer 9 proceeds to step SC, and returns the target internal resistance Rsj of the heater control circuit 31 to the first target internal resistance Rs1. With this processing, the microcomputer 9 returns the heater control by the heater control circuit 31 to the first heater control. Subsequently, the microcomputer 9 ends the series of processing steps for detection of the $H_2O$ gas concentration.

Incidentally, as compared with the case where the temperature T of the sensor section 10f is the first target temperature Tj1, blackening of the second solid electrolyte body 11 is less likely to occur when the temperature T of the sensor section 10f is higher than the first target temperature Tj1. Accordingly, if the target voltage Vj is switched from the first target voltage Vj1 to the second target voltage Vj2 before start of the second heater control of elevating the temperature T of the sensor section 10f, the voltage Vs between the first electrodes 21 and 22 is raised from the first target voltage Vj1 (450 mV) to the second target voltage Vj2 (1000 mV) in a state in which the temperature T of the sensor section 10f is the first target temperature Tj1, whereby the possibility of occurrence of blackening in the second solid electrolyte body 11 increases.

In contrast, in the present embodiment, the target voltage Vj is set to the second target voltage Vj2 with a delay after start of the second heater control. Specifically, after the heater control by the heater control circuit 31 is changed from the first heater control to the second heater control in step S3, the target voltage Vj of the comparison/PID circuit 35 is changed from the first target voltage Vj1 to the second target voltage Vj2 in step S5. As a result, the voltage Vs between the first electrodes 21 and 22 is raised from the first target voltage Vj1 to the second target voltage Vj2 after the temperature T of the sensor section 10f has become higher than the first target temperature Tj1 as a result of start of the second heater control. Therefore, as compared with the case where the target voltage Vj is set to the second target voltage Vj2 (step S5) before start of the second heater control (step S3), the possibility of occurrence of blackening in the second solid electrolyte body 11 can be decreased.

In addition, in the present embodiment, after confirming in step S4 that the temperature T of the sensor section 10f has reached the second target temperature Tj2, the target voltage Vj is set to the second target voltage Vj2 in step S5. As a result, the voltage Vs between the first electrodes 21 and 22 is raised toward the second target voltage Vj2 after the temperature T of the sensor section 10f has reached the second target temperature Tj2. Accordingly, the possibility of occurrence of blackening in the second solid electrolyte body 11 can be decreased further.

When the temperature T of the sensor section 10f is raised to the second target voltage Tj2 by the second heater control in step S3 and steps subsequent thereto, hunting (overshoot) may occur and increase the time required for the temperature T of the sensor section 10f to be stably controlled to the second target temperature Tj2. As a result, a longer time may be needed for the second pump current Ip2 to become stable.

In contrast, in the present embodiment, the microcomputer 9 confirms in step S7 that the temperature T of the sensor section 10f has become stable at the second target temperature Tj2, and then detects the second pump current Ip2 in step S9. Namely, when the microcomputer 9 raises the temperature T of the sensor section 10f to the second target temperature Tj2, the microcomputer 9 waits until the temperature T of the sensor section 10f becomes stable at the second target temperature Tj2, and detects the second pump current Ip2. Since the $H_2O$ gas concentration of the exhaust gas EG can be detected on the basis of the stable second pump current Ip2, the detection accuracy can be increased further.

Notably, in the present embodiment, the microcomputer 9 which performs the processing steps S1, S8, SD, and SE corresponds to the supply state judgment means. Also, the microcomputer 9 which performs the processing steps S5 and SB corresponds to the voltage setting means. Also, the microcomputer 9 which performs the processing step SA corresponds to the $H_2O$ gas concentration detection means.

In the above, the present invention has been described on the basis of an embodiment thereof. However, the present invention is not limited to the above-described embodiment, and may be modified without departing from the scope of the present invention. For example, in the embodiment, the gas sensor control apparatus 3 is provided between the sensor 1 and the ECU 5, and the gas sensor unit 4 is constituted by the sensor 1 and the gas sensor control apparatus 3. However, the manner of arrangement of the gas sensor control apparatus 3 can be changed freely. For example, the above-described embodiment may be modified such that the gas sensor control apparatus 3 is incorporated in the ECU 5, and the gas sensor unit is constituted by the sensor 1 and the ECU 5.

Also, in the embodiment, the gas sensor (the sensor 1) attached to an exhaust pipe is exemplified as a gas sensor. However, the present invention can be applied to a gas sensor which is attached to an exhaust pipe of an engine equipped with an EGR and which detects the concentration of a specific gas (e.g., oxygen) contained in exhaust gas, and a gas sensor control apparatus which controls the gas sensor.

DESCRIPTION OF REFERENCE NUMERALS AND SYMBOLS

1: full-range air-fuel-ratio sensor (gas sensor)
3: gas sensor control apparatus 4: gas sensor unit
5: ECU
9: microcomputer (supply state judgment means, voltage setting means, $H_2O$ gas concentration detection means)
10: sensor element
10b: detection cell
10c: pump cell
10d: heater
10f: sensor section
11: second solid electrolyte
13: first solid electrolyte
19, 20: second electrode
21, 22: first electrode
23: measurement chamber
26: heat generation resistor
30: electric circuit section
31: heater control circuit (heater control means)
32: pump current control circuit (current control means)
33: voltage detection means (current control means)
35: comparison/PID circuit (current control means)
36: pump current detection circuit (first current detection means, second current detection means)
37: internal resistance detection circuit
100: internal combustion engine system
EG: exhaust gas (object gas)
Ip: pump current
Ip1: first pump current
Ip2: second pump current
Vs: voltage between first electrodes
Vj: target voltage
Vj1: first target voltage
Vj2: second target voltage

The invention claimed is:

1. A gas sensor control apparatus configured to control a gas sensor having a sensor section and a heater for heating the sensor section, and the sensor section having (i) a detection cell which includes a first solid electrolyte body and a pair of first electrodes formed on the first solid electrolyte body, one of the first electrodes being disposed within a measurement chamber into which an object gas is introduced, and the other first electrode being exposed to an atmosphere having a reference oxygen concentration, and (ii) a pump cell which includes a second solid electrolyte body and a pair of second electrodes formed on the second solid electrolyte body, one of the second electrodes being disposed within the measurement chamber and which pumps out oxygen contained in the object gas introduced into the measurement chamber or pumps oxygen into the measurement chamber in accordance with pump current flowing between the pair of second electrodes,
the gas sensor control apparatus comprising:
a microcomputer;
current control means for controlling the pump current flowing between the pair of second electrodes;
a heater control circuit for supplying a voltage to the heater;
current detection means for detecting current flowing between the pair of second electrodes;
a minute current supply circuit for causing a current to flow between the pair of first electrodes; and
an internal resistance detection circuit for detecting an internal resistance of the first solid electrolyte body,
wherein the microcomputer comprises a CPU, ROM and RAM, and
wherein the ROM stores a control program for causing the CPU to:

control the pump current flowing between the pair of second electrodes such that a voltage produced between the pair of first electrodes becomes equal to a target voltage;
judge whether or not a supply state of the object gas is a prescribed gas supply state in which the object gas continuously has a prescribed oxygen concentration;
perform first heater control so as to control the heater such that a temperature of the sensor section becomes a first target temperature at which the sensor section becomes active, and when it is determined that that the object gas is in the prescribed gas supply state, perform second heater control so as to control the heater such that the temperature of the sensor section becomes a second target temperature higher than the first target temperature;
set the target voltage to a first target voltage at which an $H_2O$ gas contained in the object gas does not dissociate substantially, and when it is determined that the object gas is in the prescribed gas supply state, set the target voltage to a second target voltage which is higher than the first target voltage and at which an $H_2O$ gas contained in the object gas dissociates;
detect a first pump current flowing between the pair of second electrodes in a state in which the supply state of the object gas has become the prescribed gas supply state, the temperature of the sensor section has become the first target temperature, and the voltage between the pair of first electrodes has become the first target voltage;
detect a second pump current flowing between the pair of second electrodes in a state in which the supply state of the object gas has become the prescribed gas supply state, the temperature of the sensor section has become the second target temperature, and the voltage between the pair of first electrodes has become the second target voltage; and
detect the $H_2O$ gas concentration of the object gas on the basis of the first pump current and the second pump current.

2. A gas sensor control apparatus according to claim 1, wherein the gas sensor control apparatus is further configured to set the target voltage to the second target voltage with a delay after the second heater control is started.

3. A gas sensor control apparatus according to claim 2, wherein the gas sensor control apparatus is further configured to set the target voltage to the second target voltage after the temperature of the sensor section has reached the second target temperature as a result of performance of the second heater control.

4. A gas sensor control apparatus according to claim 1, wherein the gas sensor control apparatus is further configured to detect the second pump current in a state in which the temperature of the sensor section is stably maintained at the second target temperature as a result of performance of the second heater control.

5. A gas sensor system, comprising:
a gas sensor, and
a gas sensor control apparatus for controlling the gas sensor, wherein
the gas sensor comprises:
a sensor section; and
a heater for heating the sensor section,
the sensor section of the gas sensor comprises:
a detection cell which includes a first solid electrolyte body and a pair of first electrodes formed on the first solid electrolyte body, one of the first electrodes being disposed within a measurement chamber into which an object gas is introduced, and the other first electrode being exposed to an atmosphere having a reference oxygen concentration; and a pump cell which includes a second solid electrolyte body and a pair of second electrodes formed on the second solid electrolyte body, one of the second electrodes being disposed within the measurement chamber and which pumps out oxygen contained in the object gas introduced into the measurement chamber or pumps oxygen into the measurement chamber in accordance with pump current flowing between the pair of second electrodes, and the gas sensor control apparatus comprises:
  a microcomputer;
  current control means for controlling the pump current flowing between the pair of second electrodes;
  a heater control circuit for supplying a voltage to the heater;
  current detection means for detecting current flowing between the pair of second electrodes;
  a minute current supply circuit for causing a current to flow between the pair of first electrodes; and
  an internal resistance detection circuit for detecting an internal resistance of the first solid electrolyte body, wherein the microcomputer comprises a CPU, ROM and RAM, and wherein the ROM stores a control program for causing the CPU to:
  control the pump current flowing between the pair of second electrodes such that a voltage produced between the pair of first electrodes becomes equal to a target voltage;
  judge whether or not a supply state of the object gas is a prescribed gas supply state in which the object gas continuously has a prescribed oxygen concentration;
  perform first heater control so as to control the heater such that a temperature of the sensor section becomes a first target temperature at which the sensor section becomes active, and when it is determined that that the object gas is in the prescribed gas supply state, perform second heater control so as to control the heater such that the temperature of the sensor section becomes a second target temperature higher than the first target temperature;
  set the target voltage to a first target voltage at which an $H_2O$ gas contained in the object gas does not dissociate substantially, and when it is determined that the object gas is in the prescribed gas supply state, set the target voltage to a second target voltage which is higher than the first target voltage and at which an $H_2O$ gas contained in the object gas dissociates;
  detect a first pump current flowing between the pair of second electrodes in a state in which the supply state of the object gas has become the prescribed gas supply state, the temperature of the sensor section has become the first target temperature, and the voltage between the pair of first electrodes has become the first target voltage;
  detect a second pump current flowing between the pair of second electrodes in a state in which the supply state of the object gas has become the prescribed gas supply state, the temperature of the sensor section has become the second target temperature, and the voltage between the pair of first electrodes has become the second target voltage; and
  detect the $H_2O$ gas concentration of the object gas on the basis of the first pump current and the second pump current.

6. A gas sensor system according to claim 5, wherein the gas sensor control apparatus is further configured to set the target voltage to the second target voltage with a delay after the second heater control is started.

7. A gas sensor system according to claim 6, wherein the gas sensor control apparatus is further configured to set the target voltage to the second target voltage after the temperature of the sensor section has reached the second target temperature as a result of performance of the second heater control.

8. A gas sensor system according to claim 5, wherein the gas sensor control apparatus is further configured to detect the second pump current in a state in which the temperature of the sensor section is stably maintained at the second target temperature as a result of performance of the second heater control.

* * * * *